US008323203B2

(12) United States Patent
Thornton

(10) Patent No.: US 8,323,203 B2
(45) Date of Patent: Dec. 4, 2012

(54) IMAGING CATHETER

(75) Inventor: Peter Thornton, Los Altos, CA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 866 days.

(21) Appl. No.: 12/393,937

(22) Filed: Feb. 26, 2009

(65) Prior Publication Data
US 2009/0270737 A1 Oct. 29, 2009

Related U.S. Application Data

(60) Provisional application No. 61/032,348, filed on Feb. 28, 2008.

(51) Int. Cl.
*A61B 8/14* (2006.01)
(52) U.S. Cl. ........ 600/467; 600/437; 600/459; 600/462; 600/466
(58) Field of Classification Search ............... None
See application file for complete search history.

(56) References Cited

U.S. PATENT DOCUMENTS

| | | | |
|---|---|---|---|
| 4,771,774 A * | 9/1988 | Simpson et al. | 606/171 |
| 4,951,677 A | 8/1990 | Crowley et al. | |
| 5,115,814 A | 5/1992 | Griffith et al. | |
| 5,240,004 A | 8/1993 | Walinsky et al. | |
| 5,243,988 A | 9/1993 | Sieben et al. | |
| 5,284,148 A | 2/1994 | Dias et al. | |
| 5,361,768 A | 11/1994 | Webler et al. | |
| 5,383,460 A * | 1/1995 | Jang et al. | 600/439 |
| 5,503,154 A | 4/1996 | Belef | |
| 5,554,139 A | 9/1996 | Okajima | |
| 5,660,180 A | 8/1997 | Malinowski et al. | |
| 5,715,825 A | 2/1998 | Crowley | |
| 5,771,895 A | 6/1998 | Slager | |
| 5,967,984 A | 10/1999 | Chu et al. | |

(Continued)

FOREIGN PATENT DOCUMENTS

WO    WO-90/13333    11/1990
(Continued)

OTHER PUBLICATIONS

International Preliminary Report on Patentability mailed Sep. 10, 2010 for International Patent Application No. PCT/US2009/035477.

*Primary Examiner* — Long V. Le
*Assistant Examiner* — Bradley Impink
(74) *Attorney, Agent, or Firm* — Frommer Lawrence & Haug LLP; Bruce E. Black

(57) ABSTRACT

Described herein are imaging catheter system. In an exemplary embodiment, a catheter comprises a handle assembly having distal and proximal ends, a catheter sheath connected to the distal end of the handle assembly, and an elongated flexible tube connected to the proximal end of the handle assembly. The catheter further comprises an imaging core slidably received within the catheter sheath, the handle assembly and the elongated tube. The imaging core also includes a slide member, e.g., knob, extending from the imaging core and passing through an elongated slot in the handle assembly, allowing a physician to manually pullback and advance the imaging core within the catheter by sliding the slide member back and forth. Preferably, the elongated tube is long enough so that the motor drive coupled to the proximal end of the catheter is kept outside the sterile field during the imaging procedure.

13 Claims, 15 Drawing Sheets

U.S. PATENT DOCUMENTS

| | | |
|---|---|---|
| 6,013,033 A | 1/2000 | Berger et al. |
| 6,231,544 B1 * | 5/2001 | Tsugita et al. ............... 604/104 |
| 6,234,971 B1 | 5/2001 | Jang |
| 6,309,358 B1 | 10/2001 | Okubo |
| 6,413,222 B1 | 7/2002 | Pantages et al. |
| 6,592,520 B1 | 7/2003 | Peszynski et al. |
| 7,289,842 B2 | 10/2007 | Maschke |
| 2001/0021841 A1 | 9/2001 | Webler et al. |
| 2002/0007190 A1 * | 1/2002 | Wulfman et al. ............. 606/167 |
| 2002/0072704 A1 | 6/2002 | Mansouri-Ruiz |
| 2004/0049121 A1 | 3/2004 | Yaron |
| 2005/0274384 A1 | 12/2005 | Tran et al. |
| 2006/0173348 A1 | 8/2006 | Wilser et al. |
| 2006/0235299 A1 | 10/2006 | Martinelli |
| 2007/0038089 A1 | 2/2007 | Hatano et al. |
| 2007/0167821 A1 | 7/2007 | Lee et al. |
| 2007/0178717 A1 | 8/2007 | Harshman et al. |
| 2007/0282197 A1 | 12/2007 | Bill et al. |
| 2008/0041394 A1 | 2/2008 | Swann et al. |
| 2008/0065125 A1 | 3/2008 | Olson |
| 2008/0167560 A1 | 7/2008 | Thornton |
| 2008/0312536 A1 | 12/2008 | Dala-Krishna |

FOREIGN PATENT DOCUMENTS

| | | |
|---|---|---|
| WO | WO-98/15825 | 4/1998 |
| WO | WO-99/08596 | 2/1999 |
| WO | WO-00/24318 | 5/2000 |
| WO | WO-03/047673 | 6/2003 |
| WO | WO-2009/023801 | 2/2009 |

* cited by examiner

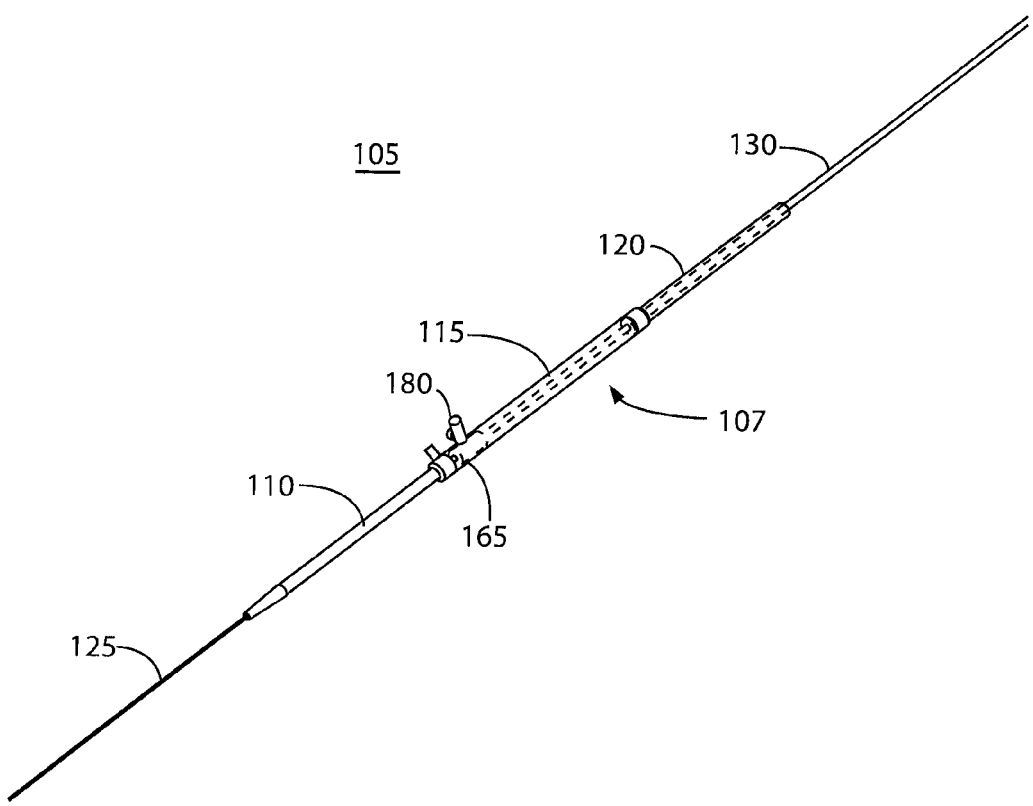

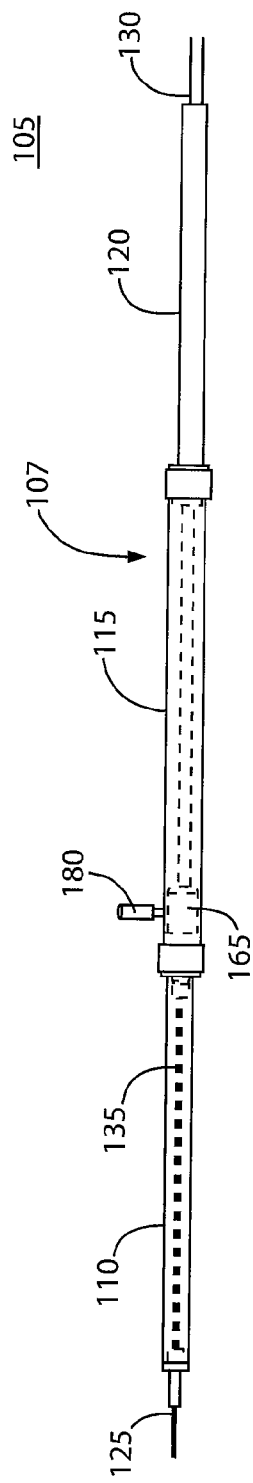
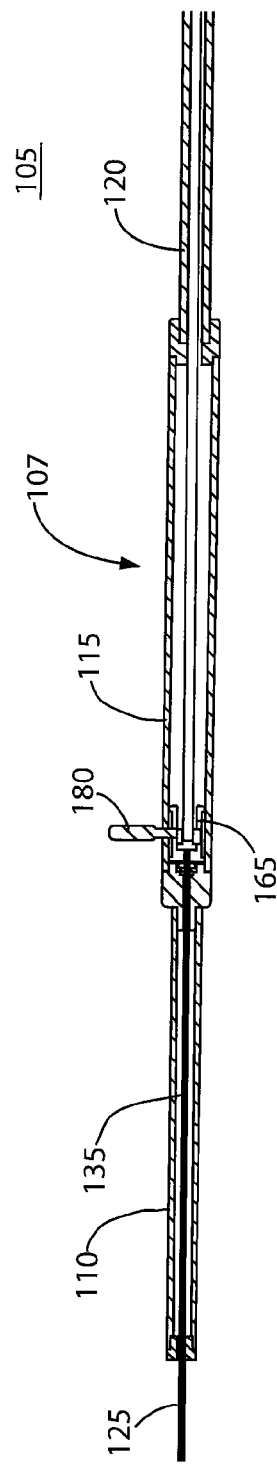

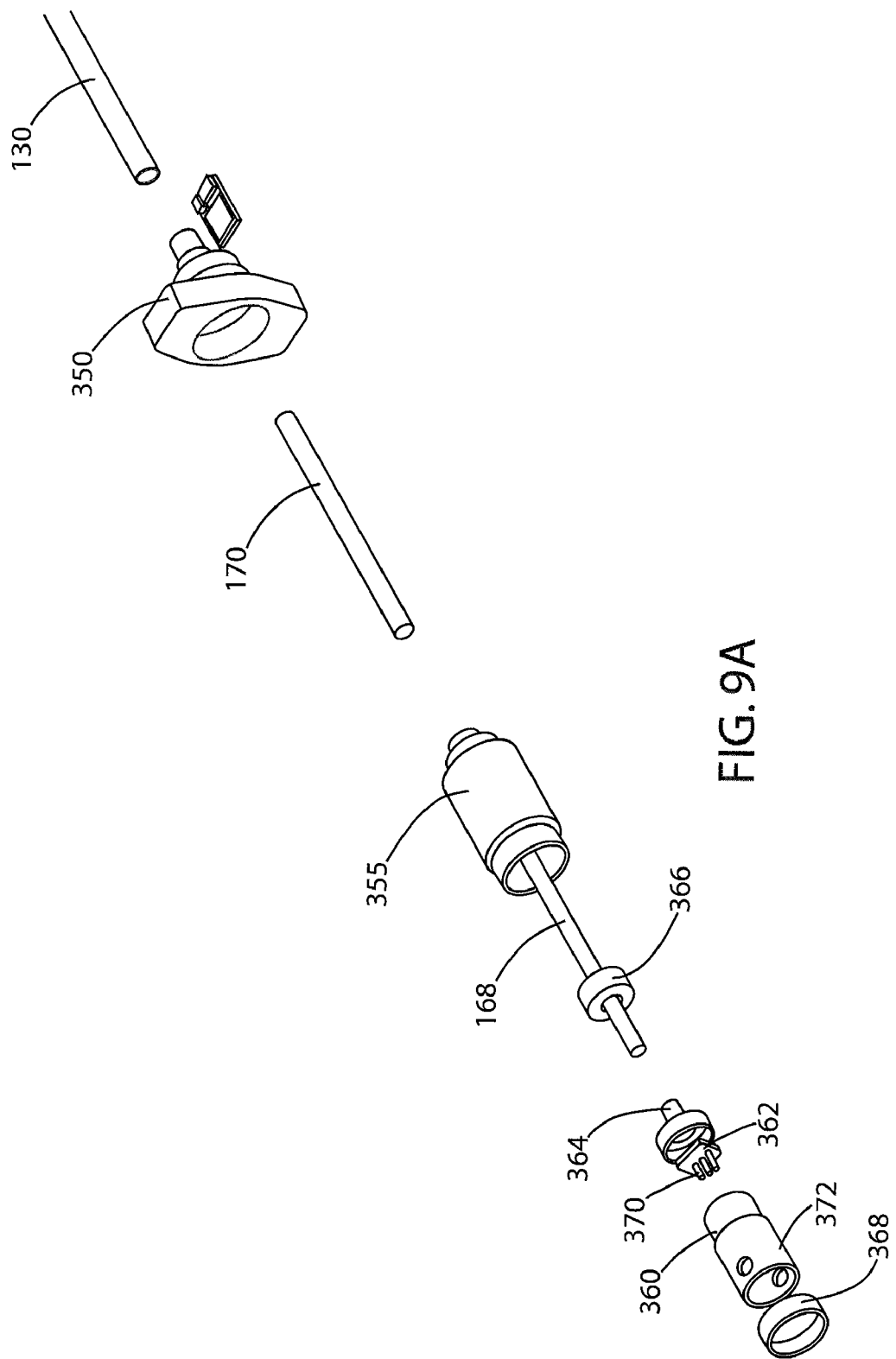

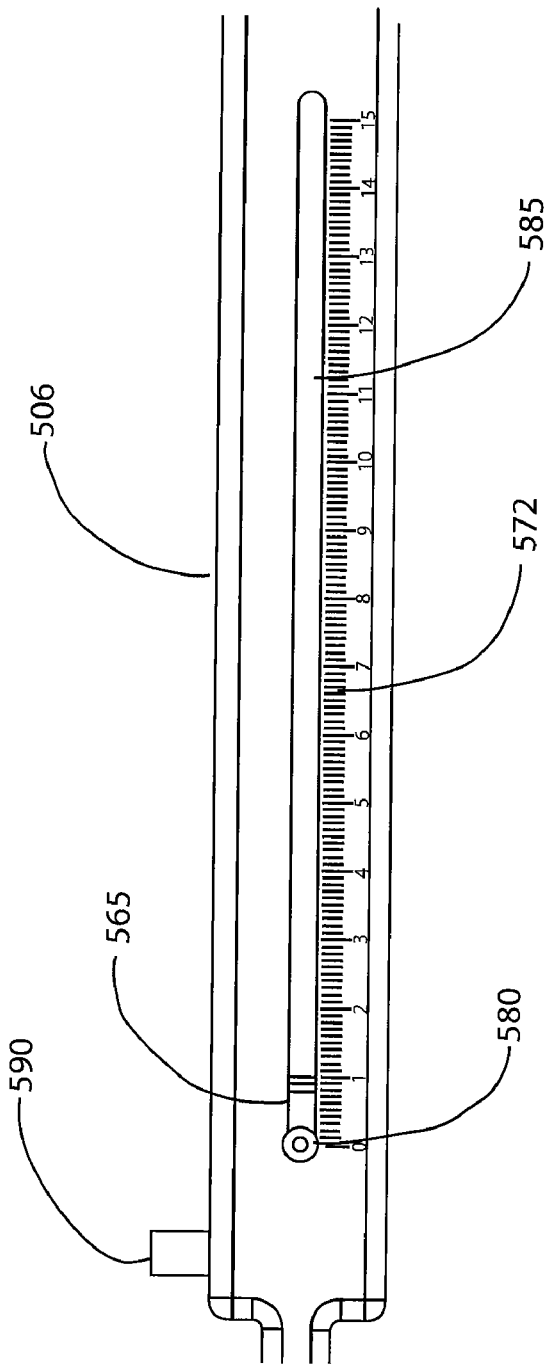
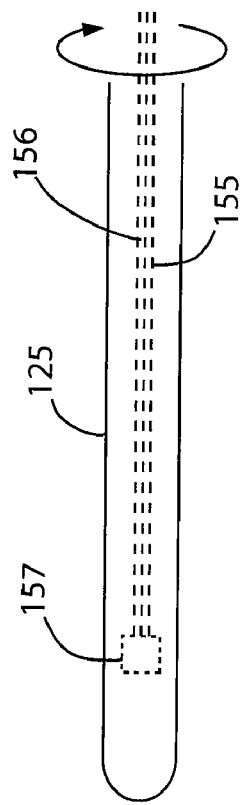
FIG. 12
FIG. 13

IMAGING CATHETER

RELATED APPLICATIONS

This application claims the benefit of U.S. Provisional Patent Application Ser. No. 61/032,348, filed Feb. 28, 2008, the entire contents of which is incorporated herein by reference.

FIELD OF THE INVENTION

The present invention relates to medical imaging, and more particularly to medical imaging catheters.

BACKGROUND INFORMATION

Intravascular ultrasound imaging systems (IVUS) are used to obtain ultrasound images inside a patient's body. An IVUS system typically includes an ultrasound catheter having a flexible catheter sheath adapted for insertion into the vascular system of the patient. To obtain ultrasound images, the catheter comprises an imaging core received within a lumen of the catheter sheath. The imaging core comprises an ultrasound transducer attached to the distal end of a long flexible drive cable and an electrical and mechanical connector at the proximal end of the drive cable. The drive cable is used to rotate and longitudinally translate the transducer within the catheter lumen to obtain images at different positions within the patient's body.

The catheter may include a telescoping section that allows the imaging core to be advanced and pulled back within the catheter sheath to image a certain distance (e.g., 150 mm) along a blood vessel. The telescoping section may comprise an outer sheath and an inner sheath that slides within the outer sheath. The electrical and mechanical connector of the imaging core is mated to a mating connector of a motor drive unit (MDU), which rotates the drive cable of the imaging core and couples electrical signals between the imaging core and an ultrasound console.

During an imaging procedure, the imaging core may be automatically pulled back within the catheter sheath by a linear motor to image along a certain distance of a blood vessel. To do this, the outer sheath of the catheter's telescoping section is held fixed by a support. The inner sheath of the catheter's telescoping section is coupled to a motor drive that is automatically pulled away from the support causing the telescoping section to expand and the imaging core within the catheter sheath to move proximally within the blood vessel. As the imaging core is pulled back, the imaging core acquires images along the blood vessel. Typically, the imaging core is advanced within the catheter sheath manually by the physician. This is because the physician can feel an obstruction as the imaging core is manually advanced, and stop advancement when the physician encounters resistance caused by the obstruction.

A physician may choose to perform a manual pullback instead of an automatic pullback. Currently, the motor drive unit must be moved back, typically by the physician's assistant, to perform the manual pullback.

Current IVUS systems suffer from several drawbacks. One drawback is that the MDU is in the sterile field and therefore must be covered, e.g., by a sterile bag, which increases the setup time. Also, the physician must handle the MDU to guide the catheter into the patient and manually advance and pullback the imaging core, which complicates the procedure and increases the risk of the MDU being accidentally dropped. Further, the MDU may get in the way of the physician during the procedure.

SUMMARY OF THE INVENTION

Described herein are imaging catheter systems that overcome drawbacks of current IVUS systems.

In an exemplary embodiment, a catheter comprises a handle assembly having distal and proximal ends, a catheter sheath connected to the distal end of the handle assembly, and an elongated flexible tube connected to the proximal end of the handle assembly. The catheter further comprises an imaging core slidably received within the catheter sheath, the handle assembly and the elongated tube. The imaging core includes a slide member, e.g., knob, extending from the imaging core and passing through an elongated slot in the handle assembly, allowing a physician to manually pullback and advance the imaging core within the catheter by sliding the slide member back and forth. Preferably, the elongated tube is long enough so that the motor drive unit (MDU) coupled to the proximal end of the catheter is kept outside the sterile field during the imaging procedure.

The catheter according to the exemplary embodiment provides several advantages over the prior art. First, the elongated tube between the handle assembly and the MDU allows the MDU to be placed outside the sterile field, which eliminates the need to place a sterile cover, e.g., bag, around the MDU and helps keep the MDU out of the physician's way during an imaging procedure. Further, the handle assembly is relatively small and light weight compared with the MDU, and thus easier to handle and maneuver during an imaging procedure. This allows the physician to more easily guide the catheter into the patient and manually advance and pullback the imaging core within the catheter.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

In order to better appreciate how the above-recited and other advantages and objects of the present inventions are objected, a more particular description of the invention briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

FIG. 1 shows perspective view of a catheter system according to an embodiment of the present invention.

FIG. 2 shows a side view of a catheter system according to an embodiment of the present invention.

FIG. 3 shows a cross-sectional view of a catheter system according to an embodiment of the present invention.

FIGS. 9a and 9b show an exploded view and a cross-sectional view, respectively, of a connector for coupling the catheter to a motor drive unit according to an embodiment of the present invention.

FIG. 12 shows a close-up view of a scale indicating the distance that the imaging core has been moved according to an embodiment of the present invention.

FIG. 13 shows an example of an ultrasound transducer attached to the distal end of the distal drive cable.

DETAILED DESCRIPTION

Figure 4:
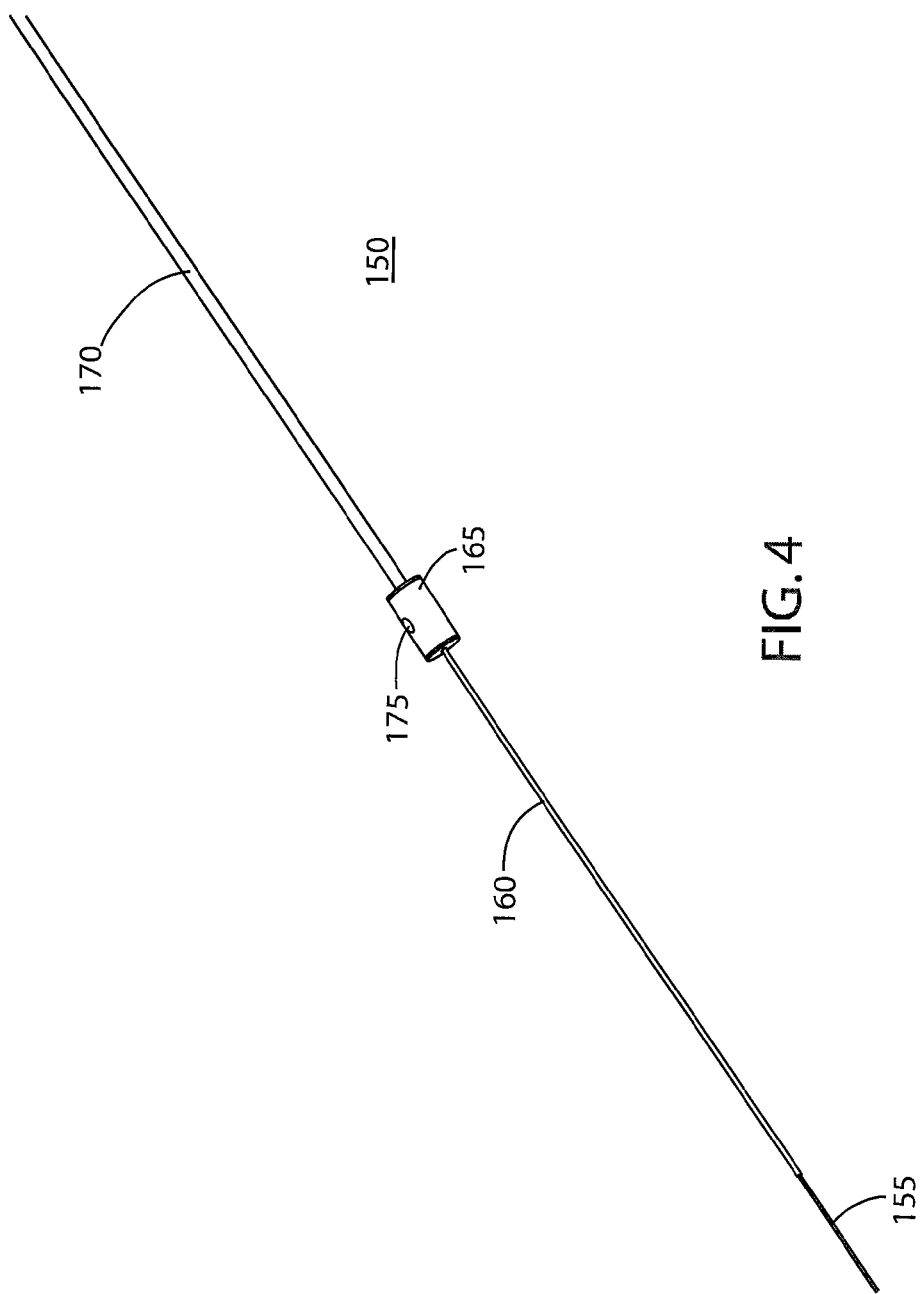
FIG. 4 shows a perspective view of an imaging core according to an embodiment of the present invention.

FIGS. 1-3 show a catheter system 105 according to an embodiment of the present invention. The catheter system 105 comprises a handle assembly 107 comprising a distal tube 110, a slotted tube 115, and a proximal tube 120. The distal and proximal tubes 110, 120 are connected to opposite ends of the slotted tube 115. The catheter system 105 further comprises a catheter sheath 125 connected to the distal end of the distal tube 110, and an outer jacket 130 connected to the proximal end of the proximal tube 120. The catheter sheath 125 is preferably an intravascular catheter sheath adapted to be inserted into a blood vessel, and may be made of a polymeric material, such as polytetrafluoroethylene (PTFE), polyethylene, PEEK, PEBAX or other suitable material. The catheter system 105 also comprises a female telescope tube 135 housed within the distal tube 110. The distal tube 110, slotted tube 115, and proximal tube 120 may be made of polycarbonate, e.g., transparent polycarbonate.

Referring to FIG. 4, the catheter system 105 also comprises an imaging core 150 that is slidably received within the catheter sheath 125, the handle assembly 107 and the outer jacket 130. The imaging core 150 comprises a small diameter distal drive cable 155 that is slidably received within the catheter sheath 125. Preferably, there is a small clearance (e.g., 0.005" inches) between the drive cable 155 and the sheath 125 to prevent kinks from developing in the drive cable 155 as the drive cable 155 is rotated. One or more ultrasound transducers may be attached to the distal end of the drive cable 155 to provide ultrasound imaging within a patient. FIG. 13 shows an example of an ultrasound transducer 157 attached to the distal end of the drive cable 155 within the catheter sheath 125, and a transmission line 156, e.g., twisted pair wires, running through the drive cable 155 for coupling the transducer 157 to an ultrasound system. The drive cable 155 is used to rotate and translate the transducer within the catheter sheath 125. Preferably, the drive cable 155 comprises two counterwound coils which has a high torsional stiffness to transmit torque to the transducer and a low bending stiffness to bend along a tortuous path of a blood vessel. The low bending stiffness is desirably since the drive cable 155 and the catheter sheath 125 are received within the patient's blood vessel and therefore have to navigate through the blood vessel. The imaging core 150 also comprises twisted pair wires (not shown) running through a lumen in the distal drive cable 155 for carrying electrical signals to and from the transducer. Alternatively, a coaxial cable or other conductor may be used for carrying the electrical signals.

The imaging core 150 further comprises a hypo tube 160 that is connected to the drive cable 155 at one end. The hypo tube 160 may be made of metal (e.g., steel) or plastic. Both the hypo tube 160 and the drive cable 155 are dimensioned to be slidably received within the female telescope tube 135 of the distal tube 110. The twisted pair wires (not shown) coupled to the transducer of the imaging core run through a lumen 162 in the hypo tube 150 (shown in FIG. 5). The imaging core 150 further comprises a slider 165 that slides within the slotted tube 115, and a slide member 180 (not shown in FIG. 4) that extends outwardly from the slider 165 and passes through an elongated slot 185 (shown in FIG. 8) in the slotted tube 115. FIG. 4 shows a hole 175 in the slider 165 into which the slide member 180 is inserted and bonded to the slider 165 during assembly. FIGS. 1-3 show the slide member 180 attached to the slider 165. The slide member 180 may comprise a knob, level or any other structure that the physician can grasp and slide back and forth. The slider 165 may be made of a lubricious plastic to facilitate sliding movement of the slider 165 within the slotted tube 115. The slide member 180 allows a physician to move the imaging core 150 longitudinally by sliding the slide member 180, as explained further below. The imaging core 150 further comprises a proximal drive cable 168 (shown in FIG. 5) covered by a drive cable cover 170. The proximal drive cable 168 may comprise two counterwound coils. Preferably, the proximal drive cable 168 has a larger diameter than the distal drive cable 155 to provide increased torsional stiffness for transmitting torque through the proximal drive cable 168. The proximal drive cable 168 can be larger than the distal drive cable 155 because the proximal drive cable 168 is not inserted into the patient, and therefore does not have to navigate the tortuous path of a blood vessel. For example, the distal drive cable 155 may have outer and inner diameters in the neighborhood of 0.0223" and 0.012" inches, respectively, while the proximal drive cable 168 may have outer and inner diameters in the neighborhood of 0.126" and 0.085" inches, respectively. In an alternative embodiment, a proximal coaxial cable may be used in placed of a counterwound proximal drive cable 168 and the drive cable cover 155. In this embodiment, the conductors of the coaxial cable provide electrical coupling while the outer jacket of the coaxial cable provides the covering.

The catheter system 105 also comprises twisted pair wires running through a lumen in the proximal drive cable 168. In the preferred embodiment, the twisted pair wires running through the proximal drive cable 168 have a larger diameter than the twisted pair wires running through the distal drive cable 155. This larger diameter reduces the amount of signal loss through the twisted pair wires of the proximal drive cable 168. The distal and proximal twisted pair wires may be soldered together in the slider 165 with an insulator covering the solder joint.

Figure 5:
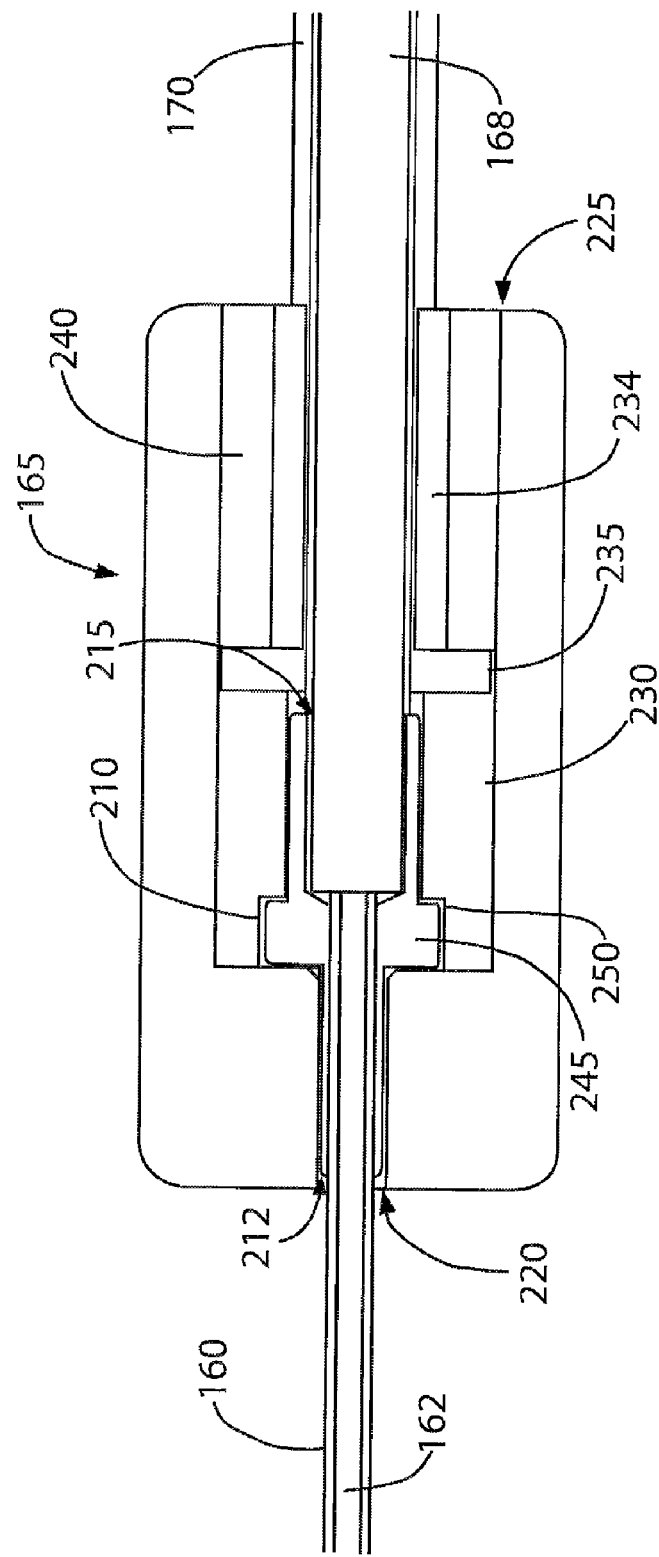
FIG. 5 shows a cross-sectional view of a slider of the imaging core according to an embodiment of the present invention.

FIG. 5 shows a cross-sectional view of the slider 165. The hypo tube 160 is connected to the proximal drive cable 168 by a coupler 210. The coupler 210 has a first hole 212 adapted to receive the hypo tube 160 and a second hole 215 adapted to receive the proximal drive cable 168. The hypo tube 160 and proximal drive cable 168 are both bonded to the coupler 210 by an adhesive (e.g., epoxy) such that the drive cable 168 and hypo tube 160 are fixed relative to each other. The coupler 210 may be made of metal or plastic.

The slider 165 has a first hole 220 adapted to rotatably receive the hypo tube 160 and a large cavity 225. The slider 165 further comprises a thrust bearing 230, a cylindrical member 234 with a retaining flange 235, and a cylindrical bushing 240, all of which are housed within the cavity 225 of the slider 165. The cylindrical member 234 with the retaining flange 235 is bonded to the drive cable cover 170 by an adhesive. The bushing 240 is bonded to the slider 165 to retain the thrust bearing 230 and the retaining flange 235 within the slider 165. The coupler 210 is rotatably received in the thrust bearing 230, allowing the hypo tube 160 and the drive cable 168 to freely rotate within the slider 165. The coupler 210 includes a circular flange 245 that fits into a corresponding circular grove 250 in the thrust bearing 230 to fix the coupler 210 longitudinally with respect to the slider 165. As a result, sliding movement of the slider 165 causes the hypo tube 160 and the drive cable 168 to move longitudinally. Thus, the hypo tube 160 and the drive cable 168 are able to rotate with respect to the slider 165 while being fixed longitudinally with respect to the slider 165 so that sliding movement of the slider 165 moves the hypo tube 160 and the drive cable 168 longitudinally.

Figure 6:
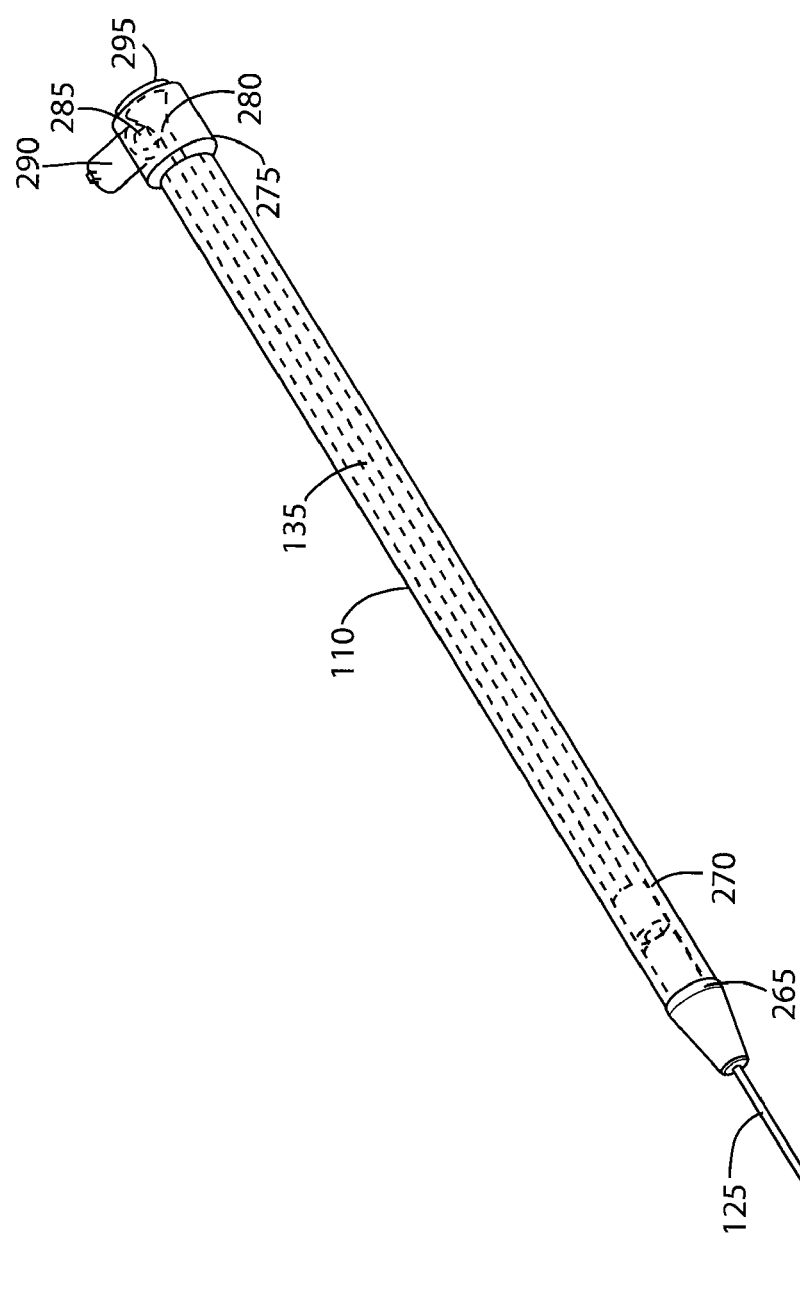
FIG. 6 shows a close up view of a distal portion of a handle assembly according to an embodiment of the present invention.

FIG. 6 shows a close-up view of the distal tube 110. The catheter system 105 further comprises a strain relief member 265 bonded to the end of the distal tube 110 for relieving strain on the catheter sheath 125. The strain relief member 265 has a tubular portion 270 that fits into the distal tube 110 and is bonded to the distal tube 110, e.g., by an adhesive. The strain relief 265 includes a lumen (not shown) extending therethough. The catheter sheath 125 and female telescope tube 135 are inserted into opposite ends of the lumen and bonded to the strain relief member 265. The distal tube 110 may be made of transparent polycarbonate, the strain relief member 265 may be made of nylon and the female telescope tube 135 may be made of Polyetheretherketone (PEEK). The catheter also comprises a cylindrical housing 275 bonded to the end of the distal tube 110. The housing 275 includes a lumen 280 extending therethrough. One end of the female telescope 135 is inserted into the lumen 280 where it is bonded to the housing 275. The catheter also comprises a flush port fluidly 285 coupled to the lumen 280, and a Luer fitting 290 coupled to the flush port 285. The flush port 285 may be used to inject a solution, e.g., saline, into the interior of the catheter sheath to provide acoustic coupling for the ultrasound transducer. The catheter also comprises a seal assembly 295 in the housing 275 for sealing the solution from the slotted tube 115. The seal assembly 295 allows the hypo tube 160 to pass through while preventing the solution from leaking out.

Figure 7:
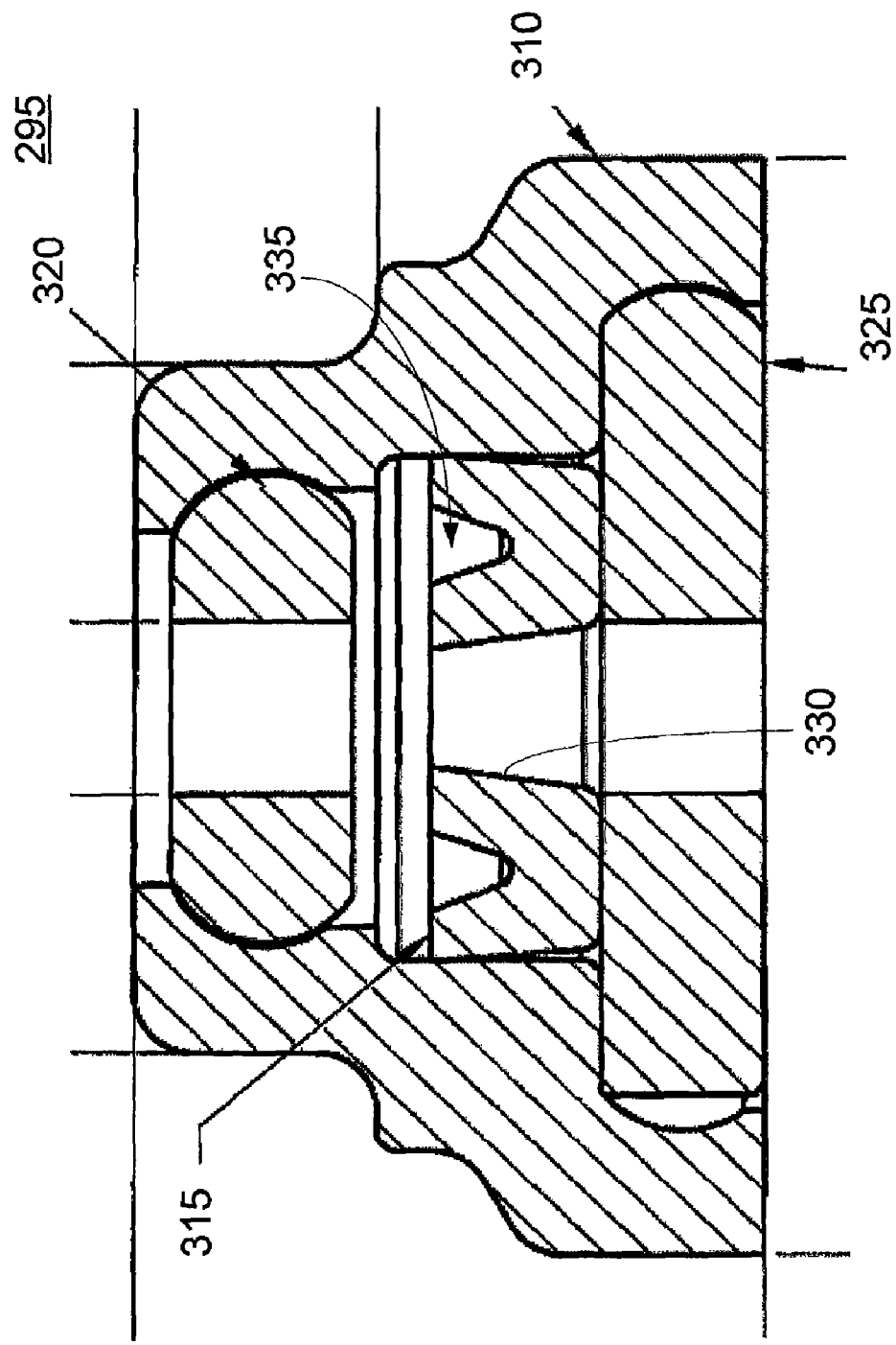
FIG. 7 shows a cross-sectional view of a seal according to an embodiment of the present invention.

FIG. 7 shows a close-up view of the seal assembly 295. The seal assembly 295 comprises a seal housing 310, a seal ring 315 and circular bearings 320,325 on opposite sides of the seal ring 315. The housing 310 may be made of polycarbonate, the seal 315 may be made of Viton or other elastomeric material, and the bearings 320,325 may be made of nylon. The hypo tube (not shown in FIG. 7) passes through holes in the center of the bearings 320, 325 and the seal 315. The holes in the bearings 320,325 are preferably centered and slightly larger than the hypo tube 160 so that the bearings 320,325 align the hypo tube 160. The seal 315 has a tapered inner surface 330 that presses against the hypo tube 160 to provide a tighter seal around the hypo tube 160. Preferably, the seal 315 is tight enough to prevent leakage while not so tight as to prevent longitudinal movement of the hypo tube 160. The seal 315 includes an inner channel 335 that receives a portion of the solution. The pressure of the solution in the inner channel 335 causes the seal ring 315 to expand, thereby tightening the seal around the hypo tube 160.

Figure 8:
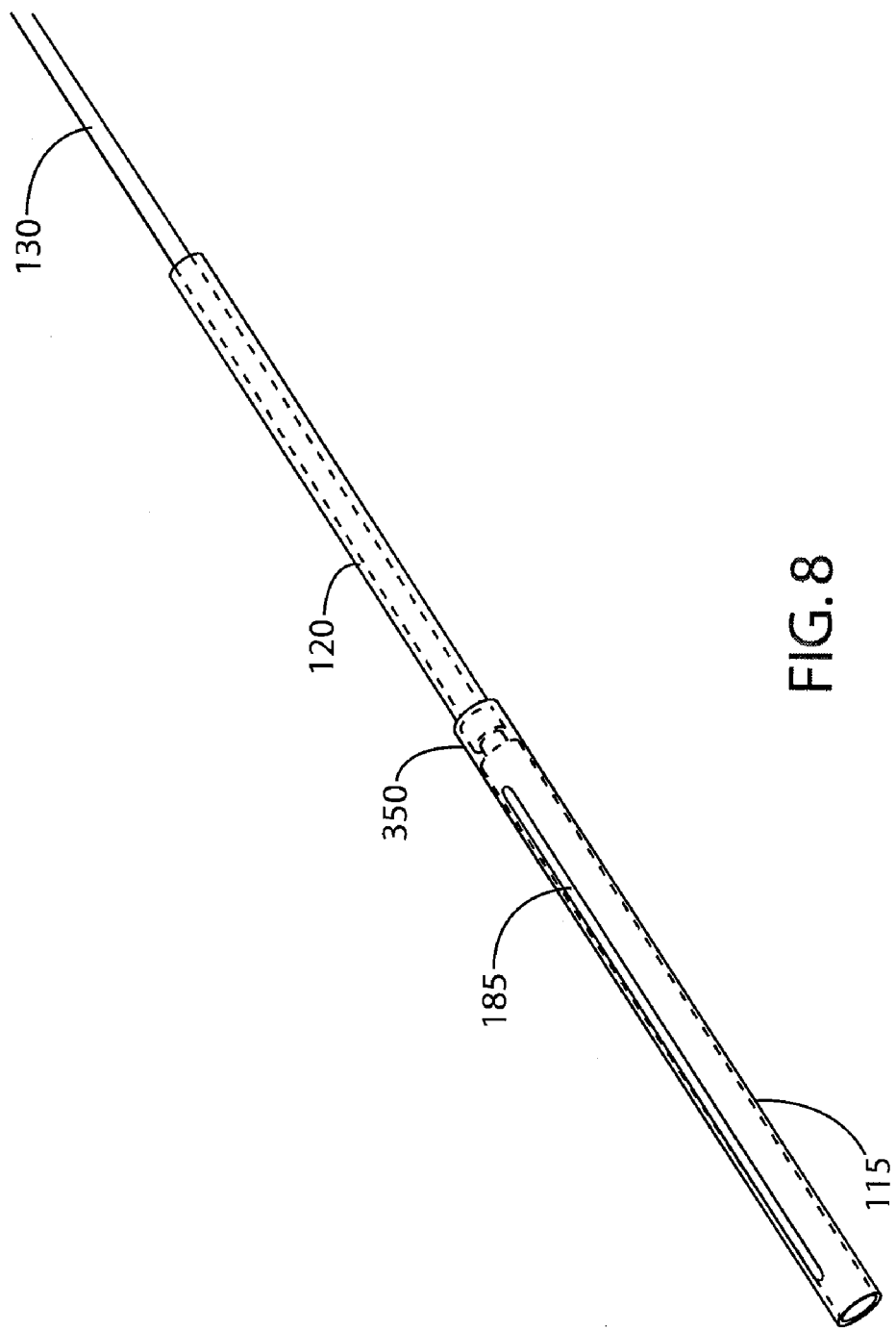
FIG. 8 shows a close up view of a proximal portion of a handle assembly according to an embodiment of the present invention.

FIG. 8 shows a close-up view of the slotted tube 115 and the proximal tube 120. The slide member 180 of the slider 165 (not shown in FIG. 8) passes through the slot 185 of the slotted tube 115. The proximal tube 120 and slotted tube 115 are bonded to a connector 350 by an adhesive, which connects the proximal tube 120 to the slotted tube 115. The outer jacket 130 is inserted through the proximal tube 120 and bonded to the proximal tube 120 and the connector 350. The proximal drive cable 168 and drive cover 170 (not shown in FIG. 8) are slidably received within the outer jacket 130. The drive cable cover 170 may comprise an etched PTFE liner overbraided with stainless steel wire and an outer layer of nylon, and have an outer and inner diameter of 0.171" and 0.131" inches, respectively. The outer jacket 130 may comprise an etched PTFE liner overbraided with stainless steel wire and an outer layer of PEBAX, and have an outer and inner diameter of 0.206" and 0.181" inches, respectively.

Figure 9B:
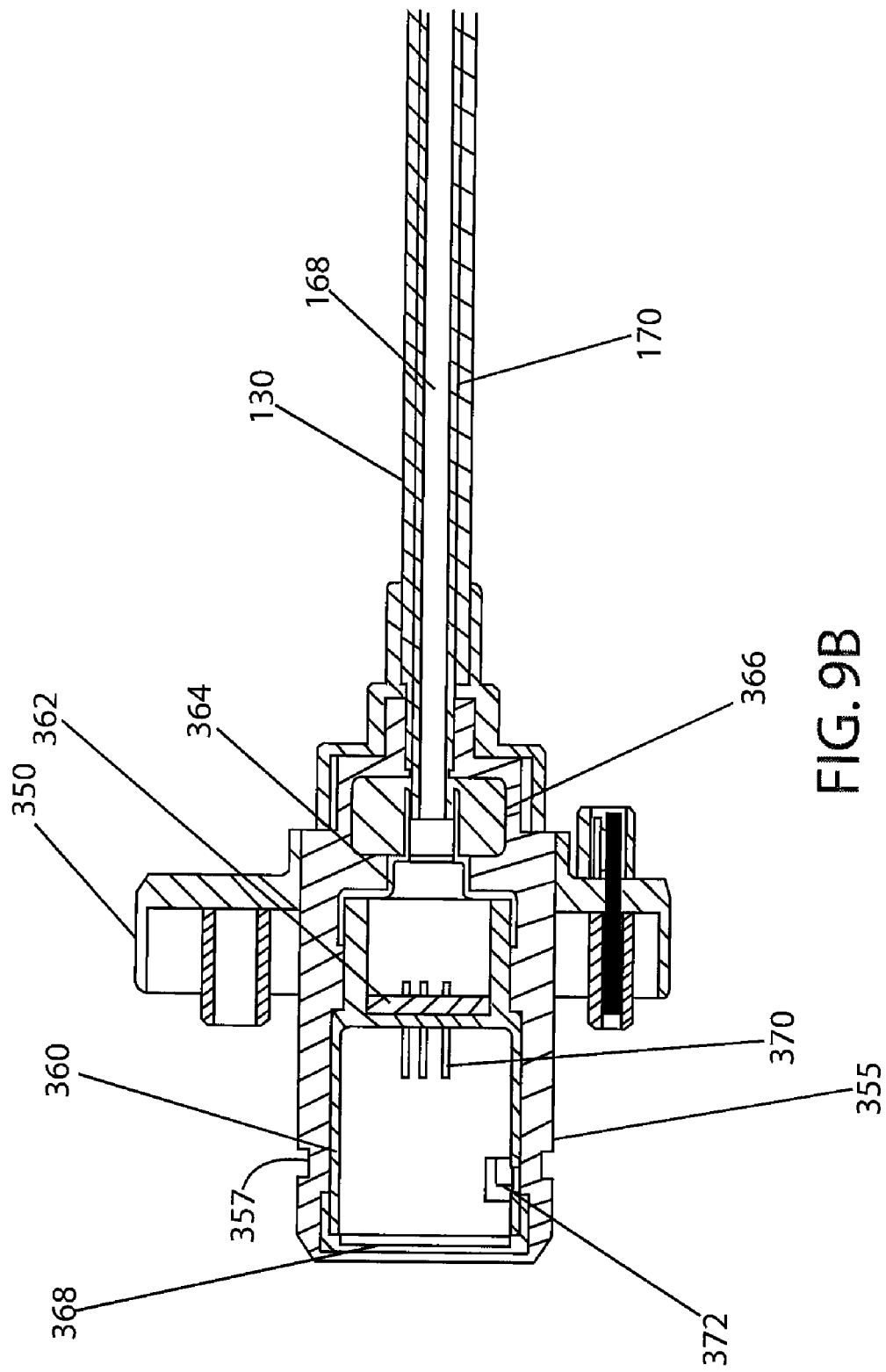

The catheter system 105 further comprises a connector at it proximal end for connecting the proximal end of the catheter to a motor drive unit (MDU). FIGS. 9a and 9b show an exploded view and a cross-sectional view, respectively, of an exemplary connector. The connector includes a connector cover 350 attached to the proximal end of the outer jacket 130, and a hub 355 attached to the proximal end of the drive cover 170. The connector further comprises rotator 360 that is rotatably housed within the hub 355 and a rotator shaft 364 that connects the proximal drive cable 168 to the rotator 360. The connector also comprises a bearing 366 and a retainer 368 for retaining the rotator 360 and the bearing 366 within the hub 355. The rotator 360 includes pins 370 or other conductors that are electrically connected to the twisted wire pairs of the proximal drive cable 168. The pins 370 may be mounted on a printed circuit board (PCB) header 362 attached to the rotator 360. The pins 370 are inserted into corresponding sockets in the MDU for electrically coupling the MDU to the transducer of the catheter. The rotator 360 may include an alignment pin 372 to align the pins 370 with the sockets of the MDU. The rotator 360 is also configured to mate to a rotary shaft of the MDU for mechanically coupling the proximal drive cable to the rotary shaft. Examples of rotators and mating connectors can be found, for example, in application Ser. No. 11/621,356 titled "Self-Aligning IVUS Catheter Rotational Core Connector," filed on Jan. 9, 2007, the entire specification of which is incorporated herein by reference. Although only a portion of the proximal drive cable 168 and cover 170 are shown in FIG. 9a, it is to be understood that the proximal drive cable 168 and cover 170 extend to the slider 165.

In a preferred embodiment, the outer jacket 130, the proximal drive cable 168, and the drive cover 170, are long enough to keep the MDU coupled to the proximal end of the catheter outside the sterile field during a medical imaging procedure. For example, they can extend a length of one or more feet. Keeping the MDU out of the sterile field simplifies preparation by eliminating the need to place a sterile bag around the MDU. This length also allows the MDU to be placed on a table or other stable surface that keeps the MDU out of the way of the physician and reduces the risk of the MDU being accidentally dropped and damaged.

During assembly, the catheter sheath 125, the distal tube 110, and the slotted tube 115 are bonded together. The imaging core 150 assembly (without the slide member 180) is fed into the slotted tube 115, the distal tube 110 and the catheter sheath 125 until the slider 165 reaches the distal end of the slotted tube 115. The proximal tube 120 and outer jacket 130 are then bonded to the proximal end of the slotted tube 115. The slide member 180 is then bonded to the slider 165 through the slot 185 in the slotted tube 115. Finally, the connector is assembled at the proximal end of the catheter.

Figure 10:
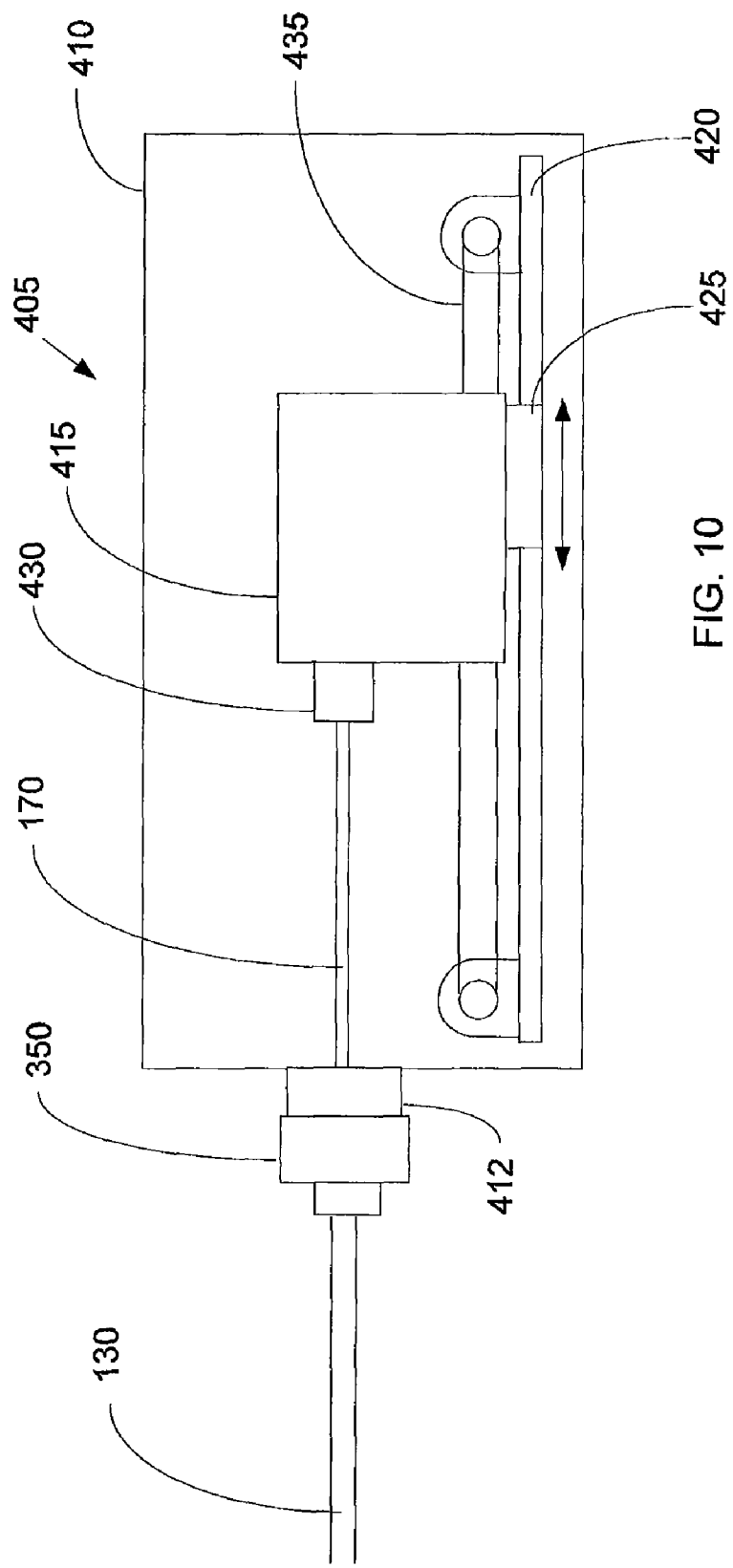
FIG. 10 shows an example of a motor drive unit that can be used with the catheter according to an embodiment of the present invention.

FIG. 10 shows a diagram of an exemplary MDU 405 that can be used with the catheter. The MDU 405 includes an outer housing 410, and a moving carriage 415 with a track slider 425 that slides on a track 420 mounted to the base of the MDU 405. The slider 425 may use slid balls to slide on the track 420 or other mechanisms that provide low friction sliding. This allows the carriage 415 to slide back and forth within the MDU housing 405. The carriage 415 houses a rotary motor (not shown) for rotationally driving the proximal drive cable 168 and an electrical coupler (not shown) for coupling electrical signals from the proximal drive cable 168 to non-rotating electronics. The electrical coupler may comprise a rotary transformer, slip rings or other means known in the art for electrically coupling rotating components to non-rotating components. The connector cover 350 connects to the housing 410 of the MDU 405. In the example shown, the connector cover 350 fits over a connecting member 412 that extends from the main body of the housing 415. The hub 355 is inserted into a connecting member 430 of the carriage 415 through an opening (not shown) in the housing 410. The connecting member 430 may include spring-biased plungers, plastic clips, or the like (not shown) that engage indents 357 on the hub 355 to secure the hub 355 to the carriage 415. The rotator 360 within the hub 355 connects to a rotary shaft in the carriage 415. This mechanically couples the proximal drive cable 168 to the rotary motor within the carriage 415. The pins 370 of the rotator 360 are inserted to sockets in the carriage 415 to electrically couple the twisted pair wires of the proximal drive cable 168 to the carriage 415.

In one embodiment, the drive cable cover 170 has enough longitudinal stiffness so that when the physician slides the slider, the drive cable cover 170 is able to push or pull the carriage 415 along the track 420. Thus, when the physician slides the slider 165 to move the imaging core longitudinally within the catheter sheath 125, the carriage 415 within the MDU 405 slides longitudinally with the imaging core. In the embodiment in which a proximal coaxial cable is used in place of the proximal drive cable 168 and drive cable cover 170, the coaxial cable preferably has enough longitudinal stiffness to slide the carriage 415.

The MDU 405 may also include a linear motor (not shown) for automatically pulling back the carriage 415, and hence the imaging core, in an automatic mode. For example, the carriage 415 may be engaged to and disengaged from a pulley 435 that runs parallel to the track 420 and is driven by the linear motor. In this example, the carriage 415 may engage (e.g., latch onto) the pulley 435 for automatic movement by the pulley 435 and disengage from the pulley 435 when the physician wishes to manually move the imaging core using the slide member 180 on the handle. A brake (not shown) or other latching mechanism may be used to engage and disengage the carriage 415 to and from the pulley 435.

The catheter according to the exemplary embodiment of the present invention provides several advantages over the prior art. First, the relatively long length of the outer jacket 130, drive cable over 170, and proximal drive cable 168 allows the MDU to be placed at a location that is outside the sterile field and out of the way of the physician. Because the MDU is outside the sterile field, there is no need to place a sterile bag around the MDU. In a preferred embodiment, the catheter is a disposable unit that comes pre-sterilized in a sterile package so that a physician does not have to sterilize the catheter before use. Further, the MDU can be placed on a table or other stable surface during a medical procedure. This eliminates the need for the physician to handle the MDU during an imaging procedure, thereby reducing the risk of the MDU being accidentally dropped and damaged. Further, the handle assembly 107 of the catheter is relatively small and light weight compared with the MDU, and thus easier to handle and maneuver during an imaging procedure. This allows the physician to more easily guide the catheter into the patient and manually advance and pullback the imaging core within the catheter.

Another advantage is that the size and weight of the MDU does not have to be minimized since the physician is not required to handle the MDU during an imaging procedure. This provides greater flexibility in the design of the MDU. For example, fans can be added for cooling and additional shielding can be added to shield the electronics from noise. Further, noise producing components can be moved farther away from sensitive areas.

Although the catheter is a disposable unit in the preferred embodiment, the catheter may comprise a disposable distal portion and a reuseable proximal portion. For example, the break between the disposable portion and the reuseable portion may come between the slotted tube and the proximal tube. This would require an additional mechanical and electrical connector for connecting the slotted tube to the proximal tube during setup. In this example, a sterile sleeve can be use to cover the reuseable portion of the catheter to maintain sterility. This embodiment has the advantage of reducing the cost of the disposable unit.

Figure 11A:
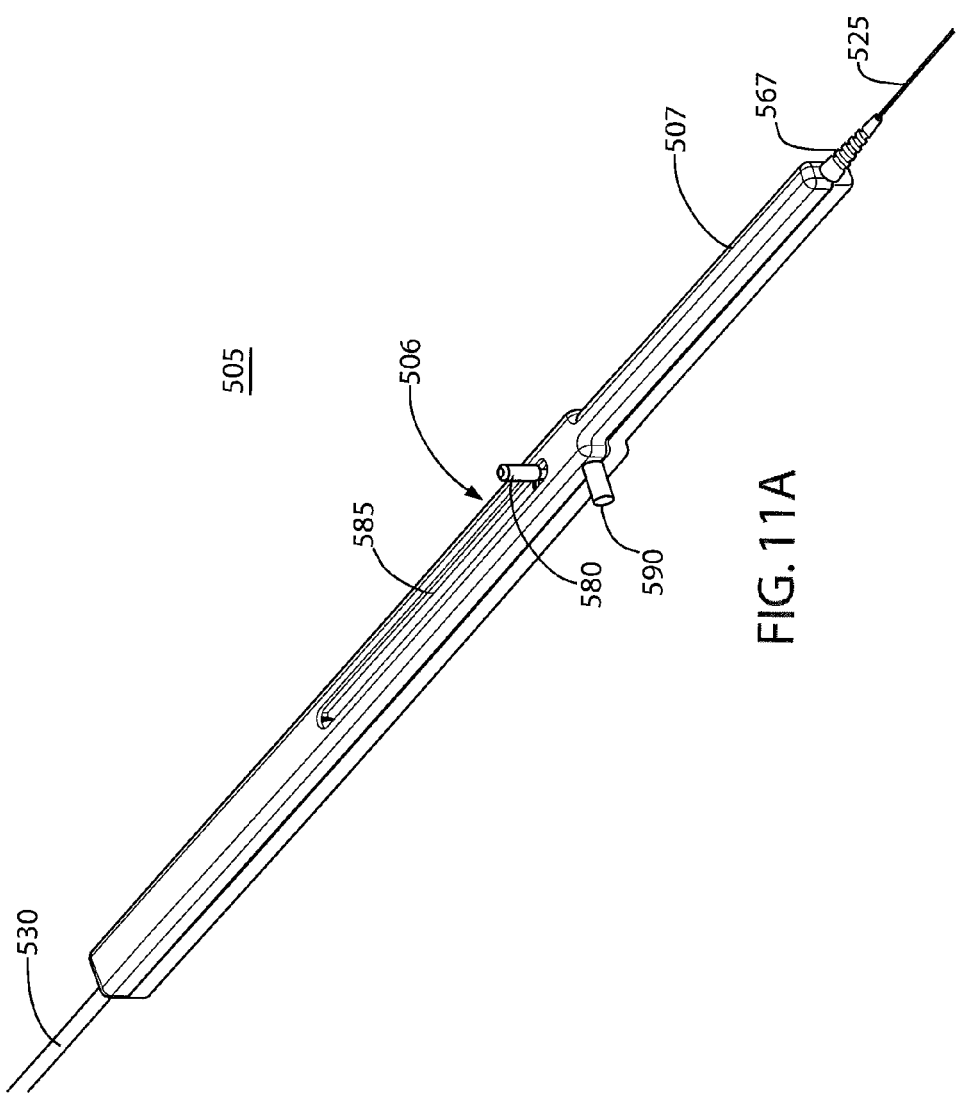
FIGS. 11a and 11b show a perspective view and an exploded view, respectively, of a catheter system in which the handle assembly comprises a clamshell according to an embodiment of the present invention.
Figure 11B:
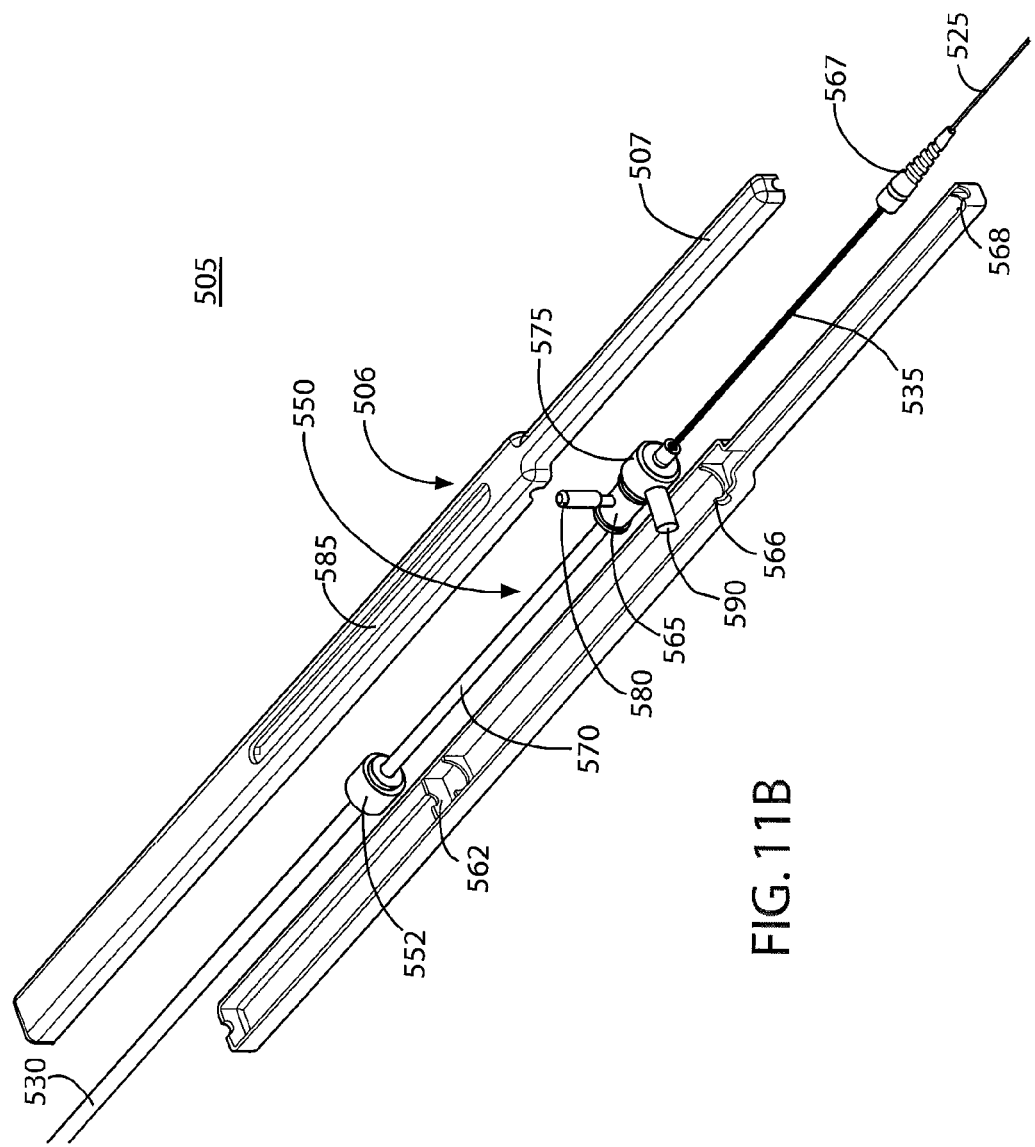

FIGS. 11*a* and 11*b* show a perspective view and an exploded view, respectively, of a catheter system 505 according to another embodiment of the present invention. In this embodiment, the handle assembly comprises a clamshell housing 506 having two pieces (shown in FIG. 11*b*) that are assembled together, e.g., by an adhesive, press-fit, snap-fit, ultra-sonic welding, or held with fasteners. The clamshell housing 506 may be made of molded plastic or other material.

The catheter also comprises a catheter sheath 525 extending distally from the clamshell housing 506, an outer jacket 530 extending proximally from the clamshell housing 506, and a strain relief 567 for the catheter sheath 525 attached to the distal end of the clamshell housing 506. The distal end of the outer jacket 530 is attached to a connector 552. The connector 552 and strain relief 567 are held in place relative to the clamshell housing 506 by holders 562 and 566, respectively, which may be molded into the clamshell housing 506. The catheter further comprises a connector housing 575, a Luer fitting 590 fluidly coupled to the connector housing 575, and a female telescope tube 535 attached at one end to the connector housing 575 and at the other end to the stain relief 567. The female telescope tube 535 is housed within a narrow portion 507 of the clamshell housing 506. The connector housing 575 is held in place within the clamshell housing 506 by holders 568, which may be molded into the clamshell housing 506.

The catheter further comprises an imaging core 550 similar to the one in the previous embodiment, and therefore not discussed in detail here for brevity. The imaging core 550 comprises a slider 565, and a slide member 580 extending outwardly from the slider 565 and passing through a slot 585 in the clamshell housing 506. The imaging core further comprises a hypo tube, a distal drive cable, a proximal drive cable, and a drive cover 570. The distal drive cable is slidably received within the catheter sheath 525 and female telescope tube 535, and the proximal drive cable and drive cover 570 are slidably received within the outer jacket 530. The catheter further comprises a MDU connector (not shown in FIGS. 11*a* and 11*b*) at the proximal end of the outer jacket 530 similar to the one in the previous embodiment, and therefore not discussed in detail here.

Similar to the catheter system in the previous embodiment, a physician can manually move the imaging core 550 longitudinally with respect to the catheter sheath 525 by sliding the slide member 580 along the slot 585. FIG. 12 shows a close-up view of the slot 585, in which a scale 572 is molded or printed along the slot 585 to indicate the longitudinal distance that the imaging core 550 has been moved.

Figure 14A:
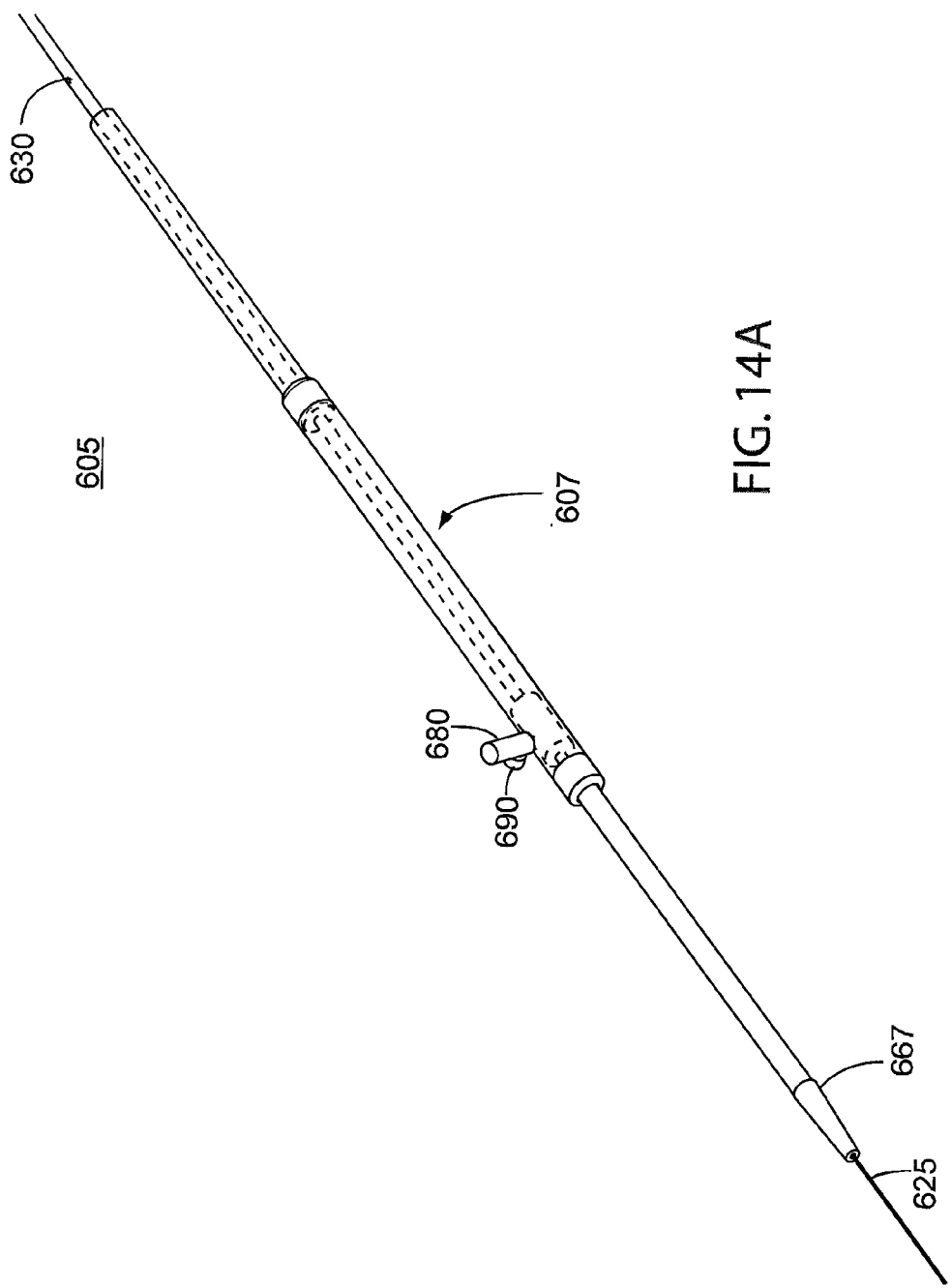
FIGS. 14a and 14b show a perspective view and an cross-sectional view, respectively, of a catheter system in which the flush port is integrated in the slider according to an embodiment of the present invention.
Figure 14B:
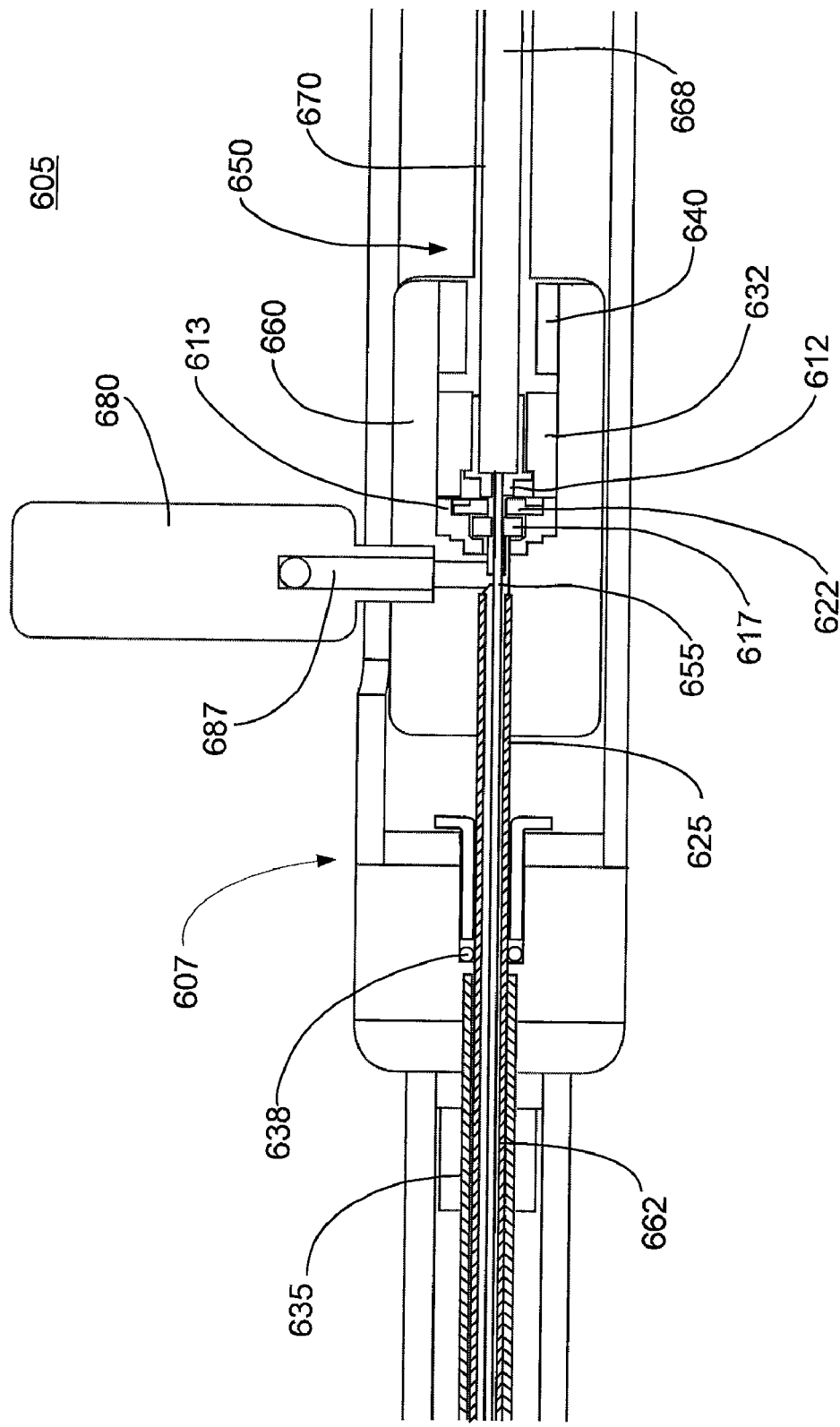

FIGS. 14*a* and 14*b* show a perspective view and a cross-sectional view, respectively, of a catheter system 605 according to another embodiment of the present invention. In this embodiment, the proximal end of the distal drive cable 655 is bonded to the coupler 612 in the slider 660. The catheter comprises a male telescope tube 662 that is slidably received within the female telescope tube 635. The male telescope tube 662, which may be made of metal or plastic, surrounds a portion of the distal drive cable 655 within the handle 607, and is bonded at its proximal end to the slider 660. The male telescope tube 662 telescopes with respect to the female telescope tube 635 to allow the imaging core 650 to move longitudinally with respect to the handle 607 and catheter sheath 625. The male telescope tube 662 passes through a seal 638 to prevent leakage.

In this embodiment, the catheter sheath 625 extends into the distal portion of the handle 607 and is slidably received between the male telescope tube 662 and the distal drive cable 655. This is done to provide additional support for the drive cable 655 and prevent kinks from developing in the drive cable 655. The catheter sheath 625 is fixed to the handle 607, e.g., by bonding the outer surface of the catheter sheath 625 to the strain relief 667.

The proximal drive cable 668 is bonded to the proximal end of the coupler 612 and extends proximally from the slider 660. The drive cover 670 is fixed to the slider 660 and also extends proximally from the slider 660. Both the proximal drive cable 668 and drive cover 670 are slidably received within the outer jacket 630 and extend proximally from the handle assembly 607 to the MDU connector (not shown in FIGS. 14*a* and 14*b*).

In this embodiment, the flush port 687 is integrated in the slider 660 with the Luer fitting 690 attached to the side of the slide member 680 (shown in FIG. 14*a*). The slider 660 includes a seal housing 613 and a seal ring 617, which forms a seal around the distal drive cable 655 to prevent leakage. A washer 622 is used to retain the seal 617 in the seal housing 613 and align the drive cable 655. The slider 660 further comprises a thrust bearing 632 for holding the coupler 612 within the slider 660 while allowing the coupler 612 to rotate within the slider 660, and a bushing 640 for retaining the thrust bearing 632 in the slider 660.

Similar to the previous embodiments, a physician can manually move the imaging core 650 longitudinally with respect to the catheter sheath 625 by sliding the slide member 680 along the slot 685. In this embodiment, the Luer fitting 690 for the flush port 687 is on the slider 660 so that the Luer fitting 690 and other components (e.g., syringe) associated with flushing move with the slider 660.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions, or a different combination or ordering of process actions. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:

1. A catheter, comprising:
    a handle having a distal end, a proximal end, a lumen between the distal and proximal ends, and a slot;
    a catheter sheath coupled to the distal end of the handle;
    an elongated tube coupled to the proximal end of the handle;
    an imaging core slidably received within the catheter sheath and the lumen of the handle, the imaging core comprising a hypo tube, a distal drive cable coupled to the hypo tube, and at least one transducer attached to a distal portion of the distal drive cable;
    a proximal drive cable received within the elongated tube and the lumen of the handle;
    a slider slidably received within the lumen of the handle, the slider defining a cavity and comprising, within the cavity, a coupler coupling the proximal drive cable and the hypo tube, a thrust bearing that rotatably receives the coupler to allow the hypo tube and proximal drive cable to freely rotate within the slider, and a bushing bonded to the slider to retain the thrust bearing within the slider; and
    a slide member extending from the slider and passing through the slot of the handle.

2. The catheter of claim 1, wherein the elongated tube extends a length of one or more feet.

3. The catheter of claim 1, wherein the elongated tube extends a length of two or more feet.

4. The catheter of claim 1, wherein the coupler has a retaining feature that is received within a grove in the slider for fixing the coupler longitudinally with respect to the slider.

5. The catheter of claim 1, wherein the distal drive cable comprises at least two counterwound coils.

6. The catheter of claim 1, wherein the proximal drive cable has a larger diameter than the distal drive cable.

7. The catheter of claim 1, wherein the proximal drive cable has an outer diameter that is at least four times larger than an outer diameter of the proximal drive cable.

8. The catheter of claim 1, wherein the slider has a flush port fluidly coupled to the cavity in the slider.

9. The catheter of claim 8, further comprising a Luer fitting attached to a side of the slider and fluidly coupled to the flush port.

10. The catheter of claim 1, wherein the handle includes a scale along the slot indicating a longitudinal position of the imaging core.

11. The catheter of claim 1, further comprising a strain relief attached to the distal end of the handle and surrounding a portion of the catheter sheath.

12. A medical system, comprising:
    a catheter, the catheter comprising:
        a handle having a distal end, a proximal end, a lumen between the distal and proximal ends, and a slot;
        a catheter sheath coupled to the distal end of the handle;

an elongated tube having a distal end, and a proximal end, wherein the distal end of the elongated tube is coupled to the proximal end of the handle;

an imaging core slidably received within the catheter sheath and the lumen of the handle, the imaging core comprising a hypo tube, a distal drive cable coupled to the hypo tube, and at least one transducer attached to a distal portion of the distal drive cable;

a proximal drive cable received within the elongated tube and the lumen of the handle;

a slider slidably received within the lumen of the handle, the slider defining a cavity and comprising, within the cavity, a coupler coupling the proximal drive cable and the hypo tube, a thrust bearing that rotatably receives the coupler to allow the hypo tube and proximal drive cable to freely rotate within the slider, and a bushing bonded to the slider to retain the thrust bearing within the slider; and a slide member extending from the slider and passing through the slot of the handle; and a motor drive unit coupled to the proximal end of the proximal drive cable.

13. The system of claim 12, wherein the motor drive unit comprises:

a motor coupled to the proximal end of the proximal drive cable; and a sliding carriage coupled to the motor and configured and arranged to slide the motor in response to movement of the slider.

* * * * *